United States Patent
Binder et al.

(10) Patent No.: US 8,133,372 B2
(45) Date of Patent: Mar. 13, 2012

(54) METHOD FOR PRODUCING CERAMIC COMPONENTS

(75) Inventors: Joachim Binder, Karlsruhe (DE); Juergen Hausselt, Germersheim (DE); Andreas Pfrengle, Bischberg (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 347 days.

(21) Appl. No.: 12/480,071

(22) Filed: Jun. 8, 2009

(65) Prior Publication Data

US 2009/0301881 A1 Dec. 10, 2009

(30) Foreign Application Priority Data

Jun. 7, 2008 (DE) .......................... 10 2008 027 323

(51) Int. Cl.
*C25D 13/02* (2006.01)
(52) U.S. Cl. ....................................................... 204/491
(58) Field of Classification Search .................. 204/491
See application file for complete search history.

(56) References Cited

U.S. PATENT DOCUMENTS

| | | | |
|---|---|---|---|
| 5,338,598 A * | 8/1994 | Ketcham | 428/210 |
| 7,655,586 B1 * | 2/2010 | Brodkin et al. | 501/103 |
| 2005/0172857 A1 * | 8/2005 | Winter | 106/35 |

FOREIGN PATENT DOCUMENTS

DE 100 49 974 A1 4/2002

* cited by examiner

*Primary Examiner* — Kishor Mayekar
(74) *Attorney, Agent, or Firm* — Venable LLP; Robert Kinberg

(57) ABSTRACT

A method for producing ceramic components, includes providing a dispersing agent comprising at least one first and one second powder fraction of an oxide ceramic, and a third powder fraction of an inter-metallic compound mixed in a liquid. The first powder fraction comprises a nanoscale particle fraction with particle sizes ranging from about 2 nm to 200 nm and functions as a binder. The second powder fraction comprises a sintering additive. The share of the third powder fraction, relative to the sum of all powder fractions, has a volume share of between about 50% and about 95%. The method further includes forming a green body with aid of precipitation by electrophoresis from the mixture, the precipitation by electrophoresis of the powder fractions occurring simultaneously. The green body is then sintered in an oxidizing atmosphere to form a ceramic component.

11 Claims, 5 Drawing Sheets

METHOD FOR PRODUCING CERAMIC COMPONENTS

CROSS-REFERENCE TO RELATED APPLICATION

This application claims the priority of German Patent Application No: DE 10 2008 027 323.6, filed on Jun. 7, 2008, the subject matter of which is incorporated herein by reference.

BACKGROUND OF THE INVENTION

The invention relates to a method for producing ceramic components that includes:
a) providing a dispersing agent consisting of at least one first and one second powder fraction of an oxide ceramic, as well as a third powder fraction of an inter-metallic compound in a liquid;
b) forming of a green body with the aid of precipitation by electrophoresis from the mixture; and
c) sintering of the green body in an oxidizing atmosphere to form a ceramic component.

In particular, the concept of the inventive method is used for producing dense ceramic molded bodies through shrinkage-reduced sintering, preferably a reaction sintering of green bodies.

Shrinkage-reduced sintering processes are distinguished in that after the sintering process, the components to be produced exhibit no change in shape or only a slight change in shape as compared to the green bodies.

The principle of the so-called reaction sintering process is based on minimizing the shrinkage occurring during the sintering process through volume-increasing reactions, e.g. oxidation reactions of metals and inter-metallic compounds. Best known among these are the RBSN (reaction bonded silicon nitride) and the RBAO (reaction bonded aluminum oxide) methods on the basis of silicon and/or aluminum. The primary disadvantage of these two methods is that the ceramic products either still contain residual porosity (in particular with the RBSN method) or, if densely sintered ceramics can be obtained through specific variants, such as SRBSN (sintered RBSN), the shrinkage can only be minimized as a result of the relatively small volume expansion and cannot be completely compensated. The reaction-sintered ceramics based on inter-metallic compounds have advantages in that case.

Shrinkage-reduced sintering methods are particularly suitable for producing prototypes or structured and/or true to form components, which require high dimensional accuracy. In particular with micro components where a subsequent processing is not possible because of the small dimensions, the reaction sintering methods distinguish themselves. However, even for the reconstruction of teeth or tooth components such as crowns or fillings, an individually formed green body should not experience any undesirable deformation during fitting operations, nor should it become larger or smaller during the subsequent sintering.

A method for producing ceramic molded bodies for use in the field of dentistry is disclosed in German patent document DE 100 49 974 A1. With this method, a green body is initially formed and is then sintered. The starting material for producing the green body is a mixture of a ceramic and a metal powder, which is then formed into a green body, preferably with the aid of precipitation by electrophoresis. The sintering occurs under oxidative conditions, wherein the metal powder is oxidized to metal oxide, which results in minimizing the sintering shrinkage. A density of more than 90% of the theoretical density is listed for the sintered ceramic component, which is not sufficient for dental use. As a result, an additional infiltration with glass particles is proposed for closing the remaining pores.

Starting with this premise, it is an object of the present invention to modify a method for producing ceramic components so that it is especially suitable for producing structures and/or true to form components. These components in particular should have a high density above 95% and preferably above 97%, so as to permit the use as mechanically and chemically stable structural ceramics, e.g. for dental applications, wherein the subsequent closing of the residual porosity with glass particles is no longer necessary.

SUMMARY OF THE INVENTION

The above an other objects are achieved according to the invention by the provision a method for producing ceramic components, comprising: providing a dispersing agent comprising at least one first and one second powder fraction of an oxide ceramic, and a third powder fraction of an inter-metallic compound mixed in a liquid, wherein the first powder fraction comprises a nanoscale particle fraction with particle sizes ranging from about 2 nm to about 200 nm and functions as a binder, the second powder fraction comprises a sintering additive, and the share of the third powder fraction, relative to the sum of all powder fractions, has a volume share of between about 50% and about 95%; forming a green body with aid of precipitation by electrophoresis from the mixture, the precipitation by electrophoresis of the powder fractions occurring simultaneously; and sintering of the green body in an oxidizing atmosphere to form a ceramic component.

By using an inter-metallic powder fraction in place of a metallic powder fraction, it is advantageously possible to sinter green bodies precipitated out by electrophoresis, which have dense and true to form dimensions, so that a later infiltration or sealing of the residual porosity is no longer required. Inter-metallic compounds are compounds that can be found between metallic and non-metallic materials because of their material characteristics (brittle, not ductile) and therefore form a separate material class. Whereas the lack of ductility of the inter-metallic compounds has a disadvantageous effect on the achievable green density when using the press-forming method, the advantage of the clearly larger relative increase in volume during the reaction sintering is fully effective during the electrophoresis, for which the ductility does not play a role. Also critical are the green densities that can be obtained with a simultaneous precipitation by electrophoresis of the so-called powder fractions and thus the absolute dimensional accuracy of the molded body following the sintering.

The oxide ceramics comprise preferably $ZrO_2$, $Al_2O_3$ and/or $SiO_2$; the inter-metallic compound preferably comprises $ZrSi_2$ and/or $ZrAl_3$, which are very easy to handle even as extremely fine powders and for which the oxidation behavior is easy to control.

One feature of the invention comprises the simultaneous precipitating out of the inter-metallic powder fraction and at least one oxidic powder fraction and preferably from a neutral suspension if a watery suspension liquid is used. The pH values are between 5 and 10, preferably between 6 and 9. With low pH values, the suspension stability is reduced because of the zeta potentials of the powders used, wherein with high pH values an increased bubble forming can be observed in the molded body, which presumably can be traced back to the forming of hydroxide, occurring in the alkaline environment, in addition to the development of hydrogen. For that reason, the use of a nearly neutral dispersing agents, e.g. DOLAPIX CE-64, is preferable to the use of acidic or alkaline dispersing agents. CE-64 has a pH value of approx. 8. The share of mixed-in dispersing agent per powder surface of all powder fractions used ranges from 200 to 4000 μg/m2, preferably from 250 to 1000 μg/m2 and especially preferred from 300 to 400 μg/m2. The effect of the dispersing agent and the neutral watery solution can also be obtained by using a non-watery solution for the suspension with the aforementioned particle fractions. However, the precipitation rates in non-watery systems are lower.

An additional feature of the invention discloses the composition and use of the first powder fraction as a binder. The first powder fraction is thus a nanoscale particle fraction with preferred particle sizes ranging from 2 to 200 nm, especially preferred from 20 to 100 nm, which is preferably precipitated out together with the inter-metallic powder fraction. The particle sizes for the inter-metallic third powder fraction range from 0.2 to 10 μm, preferably from 0.5 to 5 μm and especially preferred from 0.8 to 3 μm.

A joint precipitating out of several powder fractions, for example through membrane electrophoresis, advantageously causes a homogeneous distribution of these powder fractions throughout the green body. Especially when using nanoscale powder fractions, this method counteracts the forming of agglomerations during the processing.

Relative to the sum total of all powder fractions, the share of the third powder fraction takes up a volume share of between 50 and 95%. Each individual volume percentage share in this interval correlates to a specific reproducible sintering shrinkage, wherein the correlations depending on the composition of the suspension or the green body can be determined by conducting preliminary tests.

The first and third powder fraction preferably has a bi-modal or multi-modal size distribution, meaning the particle sizes of the powder fractions differ substantially, meaning by at least the factor of 2. The preferred ratio of average particle size of the third particle fraction to that of the first particle fraction is between 2.5 and 250 and in particular between 5 and 50.

A use of bi-modal or multi-modal powder mixtures advantageously makes possible high green densities with a share of the inter-metallic powder fraction (third powder fraction) between 50 and 90% by volume, preferably between 55 and 80% by volume and especially preferred between 60 and 75% by volume. Whereas with a low share of an inter-metallic phase, the high green densities are absolutely necessary, a higher share of an inter-metallic phase of up to 95% by volume can also lead to the goal for specific inter-metallic phases and despite a low green density.

The green densities are nearly independent of the solid-material share in the suspension, with a share of 15 to 35% by volume. The advantage of the electrophoresis is that up to a specific range, this is also true for even lower concentrations. By increasing the solid-material content (>35% by volume), the green densities can be increased again. However, an excessively high solid-material share results in excessively high viscosity, so that a useful precipitation is no longer possible. The share of solid-material in the suspension should therefore be between 1 and 60% by volume, preferably between 15 and 50% by volume and, depending on the composition, especially preferred between 25 and 35% by volume.

A specific volume share of the inter-metallic (third) powder fraction should also be adjusted for the shrinkage-reduced, preferably shrinkage-free sintering, so as to be in the range of 40 to 80%, preferably 45 to 70% and even more preferred in the range of 50 to 65% by volume (for $ZrO_2$, $Al_2O_3$ and/or $SiO_2$ as the oxide ceramic and $ZrSi_2$ as the inter-metallic compound).

The sintering behavior can be improved by mixing in the second and, if applicable, an additional powder fraction as a sintering additive. If this second powder fraction is also a nanoscale powder, it can act in the same way as the first powder fraction as binding agent and thus can also improve the green body characteristics, in particular the green body stability. As a result, the green body not only can be removed easier from the mold and is more resistant to damages, but can also be worked on prior to the sintering, e.g. by milling, lathing or other chip-removing process. The second (and if applicable the additional) powder fraction preferably comprises an oxide ceramic which as sintering additive considerably improves the molecular transport during the sintering, but also considerably improves the adhesive properties of the green body. The second (and if applicable the additional) powder fraction is completely and homogeneously bonded into the green body and/or as material component into the ceramic component during the precipitation by electrophoresis and the sintering. The share of the second powder fraction in the total volume of all powder fractions is at least 0.5% by volume. If the material is the same as a first or an additional oxide ceramic powder fraction, it is preferably at least 5% by volume and further preferred at least 10% by volume, especially preferred 20% by volume, but maximally at 50% by volume and advantageously at 45% by volume.

Particularly suitable as a sintering additive for the preferred system are $ZrO_2$, $Al_2O_3$ and/or $SiO_2$ as oxide ceramic and $ZrSi_2$ and/or $ZrAl_3$ for the inter-metallic compound, e.g. MgO which has a pronounced tendency, however, to reacting with watery solutions. Reactions of this type can be avoided by using a non-watery liquid, e.g. alcohol, as a suspension base for mixing in the powder fractions. $MgAl_2O_4$ spinel, which is preferred as the sintering additive, however, exhibits a considerable higher reaction stability in water with comparable characteristics.

With watery systems, the body is preferably formed by precipitation with the membrane electrophoresis for which the powder fractions to be precipitated out do not come in direct contact with the attracting electrodes of the electrical field in the suspension. The gas bubble formation, which occurs during the electrophoresis in watery media, therefore does not negatively influence the forming of the green body. The green body precipitated out on a membrane can be removed easily through pole reversal. The aforementioned methods reduce the mechanical forces required for unmolding, which act upon the green body, and thus significantly reduce the danger of damage or deformation of same. This effect is additionally supported by drying or hydrophobizing of the membrane, which can thus be separated easier from the green body. A drying of the precipitated out green body, e.g. in the super-critical range, can also result in defect-free components.

With these reaction-sintered oxidation ceramics, e.g. the system $Al_2O_3$—$SiO_2$—$ZrO_2$, the sintering temperature, depending on the composition as well as the type and amount of sintering additives used, ranges from 1200 to 1650° C. and preferably from 1400 to 166° C., especially preferred from 1450-1575° C.

BRIEF DESCRIPTION OF THE DRAWINGS

These and other features and advantages of the invention will be further understood from the following detailed description of embodiments of the invention with reference to the accompanying drawings, showing in:

FIG. 9 The zeta potentials of suspensions with alternative inter-metallic powder fractions in dependence on the pH values, analog to FIG. 4a.

DETAILED DESCRIPTION

Exemplary Embodiment

Figure 1:
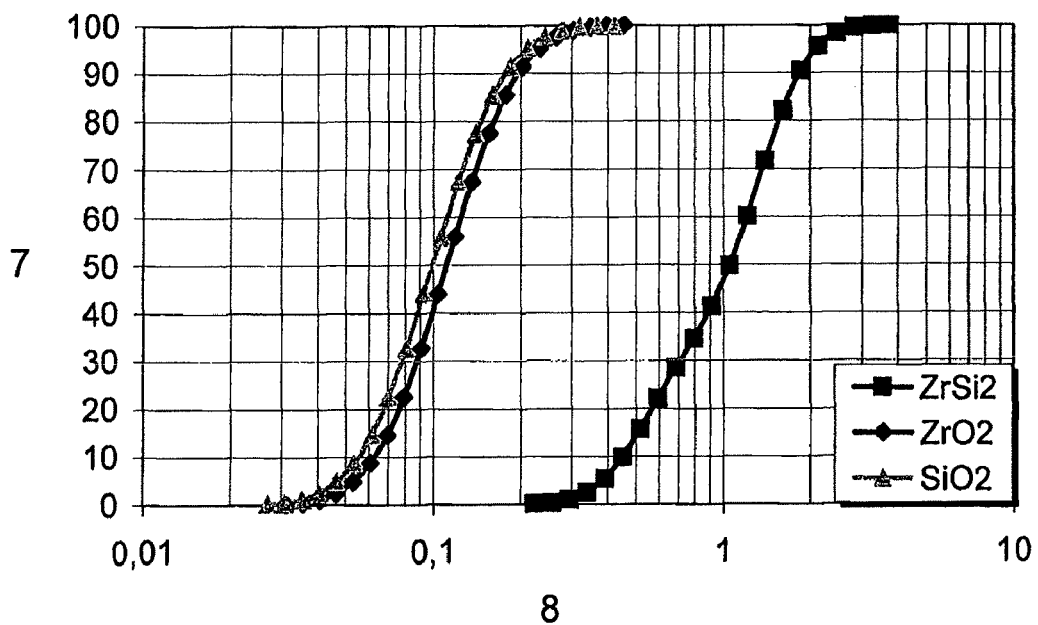
FIG. 1 The particle size distribution (volume percentage to particle diameter) for example of $ZrSi_2$, $ZrO_2$ and $SiO_2$ suspensions.

For the precipitating out by electrophoresis of green bodies, several suspensions comprising powder fractions having the following solid material components (materials) were prepared:

$ZrSi_2$ (Co. H.C. Starck)
$ZrO_2$, Tz-O (monocline), (Co. Tosoh)
$SiO_2$, Aerosil OX 50 (Co. Degussa)
MgO (Co. Merck)
$Al_2O_3$, γ-oxide of aluminum (Co. Merck)
$MgAl_2O_4$ magnesium-aluminum oxide 99.985% (Co. Alfa Aesar)

$ZrSi_2$, $ZrO_2$ and optionally also the nanoscale SiO2 as inorganic binder are primarily used for producing the suspensions while the remaining materials serve as sintering additives. Table 1 shows the densities and the mol masses of the aforementioned solid material components. The powder fractions are dispersed in de-ionized water (DI water). The suspensions are stabilized either by adding tetra-methyl ammonium hydroxide (TMAH; 25 weight % solution in water; Co. Sigma Aldrich) or DOLAPIX CE 64 (Co. Zschimmer & Schwarz) as dispersing agent, which has an active substance concentration of 65% and a density of 1.2 g/m$^3$.

TABLE 1

| Material data for the starting materials used | | | | | | |
|---|---|---|---|---|---|---|
| | $ZrSi_2$ | $ZrO_2$ | $SiO_2$ | MgO | $Al_2O_3$ | $MgAl_2O_4$ |
| density g/cm$^3$ | 4.88 | 5.83 | 2.20 | 3.58 | 3.94 | 3.60 |
| mol weight g/mol | 147.40 | 123.22 | 60.08 | 40.30 | 101.96 | 142.27 |

TABLE 1-continued

At the time of delivery, the $ZrSi_2$ used has a BET surface of 1.83 m$^2$/g, an average particle size $d_{50}$ of 3.02 µm and a mass increase of 62.70%. According to the analysis certificate, the powder consists of 37.5 weight % Si; 0.8 weight % O; 0.16 weight % C; 0.13 weight % N and 0.083 weight % Fe.

The $ZrSi_2$ is ground up in Isopropanol inside an agitated ball mill. The agitating container, which is lined with ZrO2, is filled with $Y_2O_3$ stabilized $ZrO_2$ grinding balls having a diameter of 0.8 mm. The $ZrSi_2$ powder charges produced for the purpose of this embodiment for producing the green body are henceforth referred to as FM017 and FM018.

Also used for the green body production are two $ZrO_2$ charges (Z001889P and Z005551P), for which the specific surfaces were also determined.

The increase in mass of the $ZrSi_2$ powder, determined with the thermo-gravimetric method prior to the grinding, is theoretically 65.13%. Prior to being used for the precipitation by electrophoresis, the powder is furthermore tempered for one hour at 400° C. (heating rate 5 K/min, cooling rate 10 K/min) to remove organic residues.

Before mixing the powder fractions into a prepared liquid provided with a dispersing agent and/or a TMAH base (TMAH—tetra-methyl ammonium hydroxide) to form a suspension (dispersing agent DI water), these fractions were weighed and subsequently mixed in the dry state before adding them to the liquid. Adding the powder fractions to the liquid occurs over a period of 2 to 15 minutes, depending on the solid material content. The suspension is then stirred, preferably for about 30 minutes, which is followed by an additional dispersion with the aid of ultrasound. Owing to the dissipated ultrasound effect, the suspension is cooled in an ice water bath to avoid any heating up.

FIG. 1 shows the particle-size distributions (volume share 7 in [%] over the particle diameter 8 in [µm]) CE 64 stabilized, single-phase $ZrSi_2$ (zirconium disilicid), $ZrO_2$ (zirconium oxide) and $SiO_2$ suspensions (silicon dioxide; nanoscale) (acoustic measuring method). The $ZrSi_2$ powder fraction represents the third powder fraction, the $ZrO_2$ and $SiO_2$ powder fractions represent the first and, if applicable, an additional powder fraction. The $ZrSi_2$ and the $ZrO_2$ suspensions for the acoustic measuring method are produced with a solid content of 35% by volume while the $SiO_2$ suspensions only have half the solid content (17.5% by volume) because of the dispersion difficulty. The dispersing agent content of the suspensions used for the PSD measurements is selected high enough so that there is always a sufficient amount of dispersing agent for a complete surface coverage of the particles. The $d_{50}$ values for $ZrO_2$ and $SiO_2$ are approximately at 100 to 130 nm and for $ZrSi_2$ at 1.1 µm. The $d_{90}$ values for $SiO_2$ are at approx. 200 nm and for $ZrSi_2$ at approx. 2 µm. A $d_{90}$ value for $ZrO_2$ cannot be determined with certainty because of the differing measuring data. However, it can be said approximately that the particles of the $ZrSi_2$ powder are larger by the factor 10 than those of the two other powders.

Figure 2:
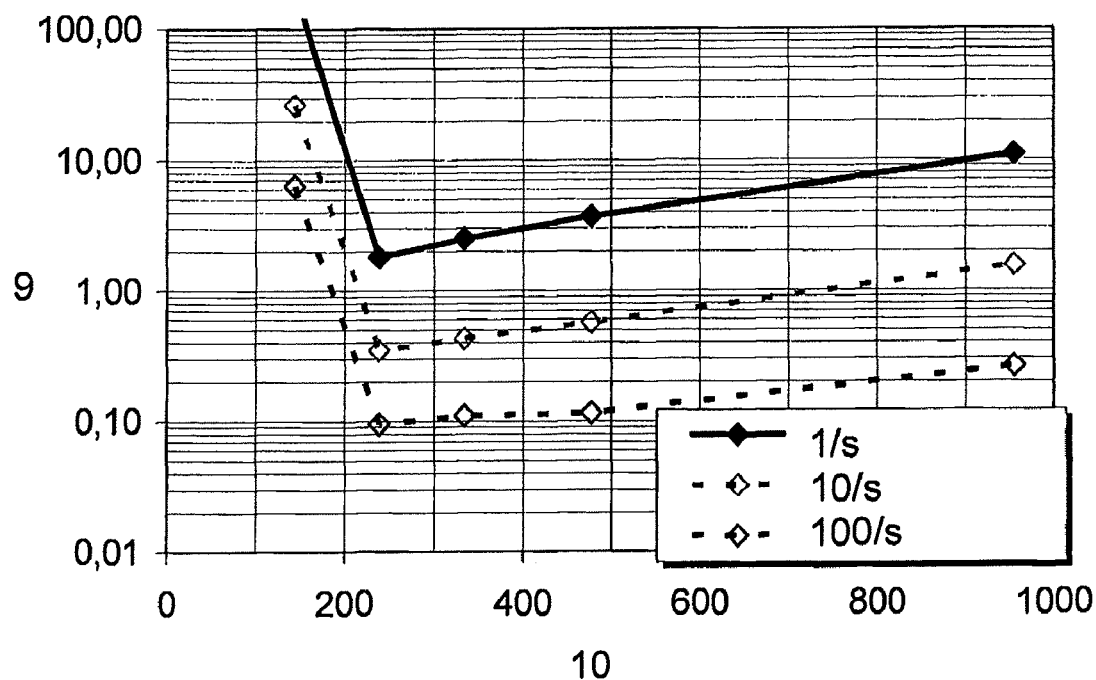
FIG. 2 The viscosity course over the dispersing agent share at different shearing rates in a rheological analysis of a 45% by volume suspension (59:31:10% by volume $ZrSi_2$:$ZrO_2$:$SiO_2$)

Rheological analyses are used to determine the optimum dispersing agent content in the suspensions. FIG. 2 shows the viscosity 9 in [Pas] plotted over the dispersing agent share CE-64 10 in [µm/m$^2$] for the various shearing rates 1/s; 10/s;

and 100/s, wherein mixtures of the three powder fractions were used for the measurements. To observe a clear influence on the viscosity, the measurements were realized with 45W by volume suspensions. The suspensions are composed of $ZrSi_2:ZrO_2:SiO_2$ at a ratio of 59:31:10% by volume. The surface coverage for this mixture preferably is at least 250 µg/m². A higher dispersing agent content leads to a slightly higher viscosity. A dispersing agent content of 300 to 400 µm/m² is preferred to ensure that the dispersing agent content is always sufficiently high, meaning also in the case of separations. For the presently used mixture, this corresponds to a dispersing agent content of 0.35% by weight relative to the powder mass.

Figure 3:
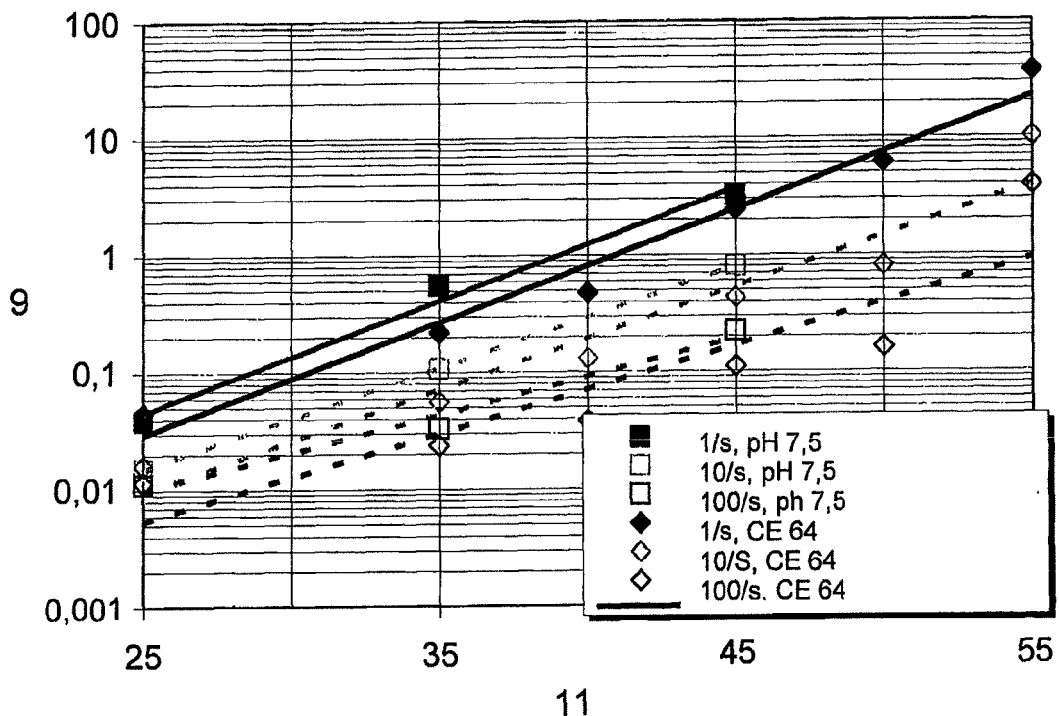
FIG. 3 The viscosity of the suspension in dependence on the solid material content;
the powder mixture composition is 59:31:10% by volume $ZrSi_2$:$ZrO_2$:$SiO_2$; the stabilization occurs through TMAH (pH 7.5) and/or CE 64 (350 µg/m$^2$)

FIG. 3 shows the viscosity 9 in [Pas] plotted over the solid material content 11 in [vol %] for the various shearing rates 1/s, 10/s and 100/s. The viscosity of a suspension increases exponentially with the increase in the solid material content. In addition to the stabilization with CE 64, the stabilization with a slight amount of TMAH at a pH value of 7.5 is also given in this case. When comparing the viscosity values, it is obvious that the stabilization with TMAH in part leads to clearly higher viscosities than with CE 64.

Figure 4A:
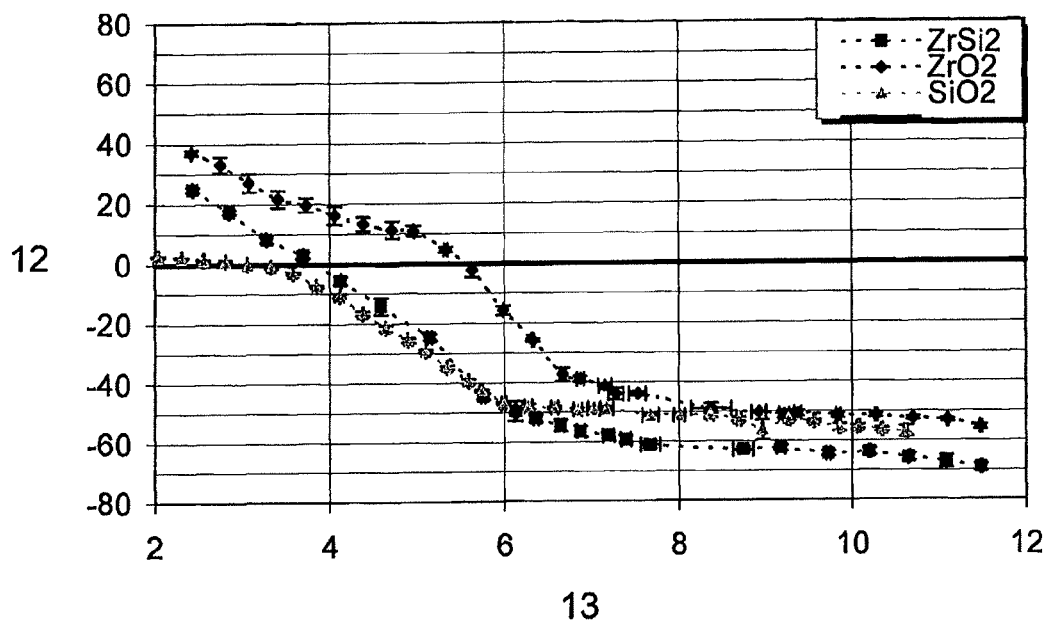
FIGS. 4a and 4b The zeta potential courses of $ZrSi_2$, $ZrO_2$ and $SiO_2$ suspensions in dependence on the pH values (a) and dispersing agent share (b)

Besides the particle size distribution and the rheological properties of the suspension, the zeta potential of the particles is extremely important. FIG. 4a reflects the zeta potential 12 in [mV] plotted over the pH value 13, without the admixture of a dispersing agent. Whereas a weak positive zeta potential is present in the acid range, it is relatively stable between −40 and −60 mV starting with a pH value of approximately 7. The iso-electric points are located at approximately 3.4 and 5.5 for $SiO_2$, $ZrSi_2$ and $ZrO_2$.

Figure 4B:
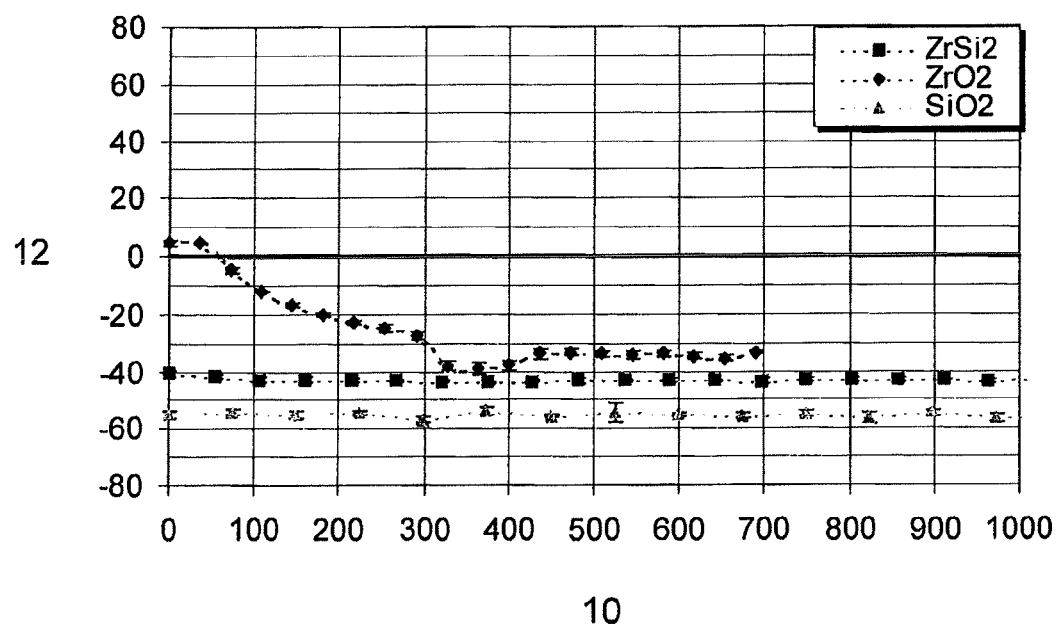

FIG. 4b on the other hand shows the course of the zeta potential 12 in [mV] plotted over the dispersing agent content CE-64 10 in [µg/m²]. Both, $ZrSi_2$ and $SiO_2$ already have a negative zeta potential, without the admixture of a dispersing agent, while $ZrO_2$ requires a certain amount, at least 100 and preferably 350 µg/m², of dispersing agent to ensure a negative zeta potential. The dispersing agent is deposited on the surface, thereby changing the surface charge and thus also the zeta potential. The pH values for the highly diluted suspensions without dispersing agent range from approximately 6 to 7.

The pH values and the specific electrical conductivity values of the suspensions are furthermore recorded (see Table 2 below) based on the particle size distributions shown in FIG. 1. The characteristic values for a suspension of a mixture resulting in nearly shrinkage-free molded bodies can additionally be found there, wherein this mixture is composed of 61:32:5:2% by volume $ZrSi_2:ZrO_2:SiO_2:MgAl_2O_4$. With this suspension, the average values and standard deviations of five different suspensions are provided, which have a similar (not identical) composition. It must furthermore be taken into account that the $SiO_2$ suspension contains a high amount of dispersing agent because of the large BET surface.

TABLE 2

Shows the pH values and conductivities.
Shrinkage-free consists of 61:32:5:2 % by volume
$ZrSi_2:ZrO_2:SiO_2:MgAl_2O_4$.

|  | pH values | conductivity (S/m) |
|---|---|---|
| 35% by volume $ZrSi_2$ | 7.52 | 0.1084 |
| 35% by volume $ZrO_2$ | 8.53 | 0.1450 |
| 17.5% by volume $SiO_2$ | 8.68 | 0.3003 |
| shrinkage-free | 8.06 ± 0.30 | 0.1071 ± 0.0100 |

The following Table 3 provides a summary of all embodiments described in the following for the green density.

TABLE 3

Composition and molar ratio of the analyzed suspensions as well as the green densities of the green bodies produced with these suspensions.

| No. | solid % vol. | composition ZrSi₂ % vol. | ZrO₂ % vol. | SiO₂ % vol. | molar ratio Zr/Si | theoretic Zr/Si | green density theoretic g/cm³ | absolute g/cm³ | relative % p. dev. |
|---|---|---|---|---|---|---|---|---|---|
| 1 | 35% | 0% | 100% | 0% | inf. | 5.830 | 3.267 | 56.04% | 0.24% |
| 2 | 35% | 30% | 70% | 0% | 2.170 | 5.546 | 3.366 | 60.68% | 0.04% |
| 3 | 35% | 50% | 50% | 0% | 1.214 | 5.356 | 3.355 | 62.64% | 0.13% |
| 4 | 35% | 60% | 40% | 0% | 0.976 | 5.262 | 3.348 | 63.63% | 0.09% |
| 5 | 35% | 65% | 35% | 0% | 0.885 | 5.215 | 3.326 | 63.78% | 0.17% |
| 6 | 35% | 70% | 30% | 0% | 0.806 | 5.167 | 3.303 | 63.92% | 0.22% |
| 7 | 35% | 75% | 25% | 0% | 0.738 | 5.120 | 3.259 | 63.65% | 0.13% |
| 8 | 35% | 80% | 20% | 0% | 0.679 | 5.073 | 3.186 | 62.81% | 0.17% |
| 9 | 35% | 90% | 10% | 0% | 0.579 | 4.977 | 3.040 | 61.08% | 0.17% |
| 10 | 35% | 100% | 0% | 0% | 0.500 | 4.883 | 2.878 | 58.93% | 0.08% |
| 11 | 35% | 0% | 90% | 10% | 11.630 | 5.467 | 3.087 | 56.47% | 0.36% |
| 12 | 35% | 30% | 60% | 10% | 1.628 | 5.183 | 3.087 | 59.56% | 0.17% |
| 13 | 35% | 50% | 40% | 10% | 0.965 | 4.994 | 3.114 | 62.37% | 0.05% |
| 14 | 35% | 60% | 30% | 10% | 0.785 | 4.899 | 3.103 | 63.35% | 0.11% |
| 15 | 35% | 70% | 20% | 10% | 0.653 | 4.805 | 3.083 | 64.17% | 0.05% |
| 16 | 35% | 80% | 10% | 10% | 0.551 | 4.709 | 3.002 | 63.74% | 0.05% |
| 17 | 35% | 90% | 0% | 10% | 0.471 | 4.615 | 2.880 | 62.41% | 0.35% |
| 18 | 35% | 0% | 80% | 20% | 5.170 | 5.104 | 2.860 | 56.03% | 0.16% |
| 19 | 35% | 24% | 56% | 20% | 1.485 | 4.877 | 2.819 | 57.80% | 0.10% |

TABLE 3-continued

Composition and molar ratio of the analyzed suspensions as well as the green densities of the green bodies produced with these suspensions.

| No. | solid % vol. | ZrSi$_2$ % vol. | ZrO$_2$ % vol. | SiO$_2$ % vol. | molar ratio Zr/Si | theoretic Zr/Si | green density theoretic g/cm$^3$ | green density absolute g/cm$^3$ | relative % p. dev. |
|---|---|---|---|---|---|---|---|---|---|
| 20 | 35% | 48% | 32% | 20% | 0.793 | 4.649 | 2.857 | 61.45% | 0.02% |
| 21 | 35% | 56% | 24% | 20% | 0.673 | 4.574 | 2.892 | 63.23% | 0.14% |
| 22 | 35% | 64% | 16% | 20% | 0.579 | 4.498 | 2.887 | 64.17% | 0.24% |
| 23 | 35% | 72% | 8% | 20% | 0.502 | 4.422 | 2.865 | 64.80% | 0.13% |
| 24 | 35% | 80% | 0% | 20% | 0.439 | 4.346 | 2.825 | 64.99% | 0.33% |
| 25 | 15% | 70.4% | 29.6% | 0% | 0.800 | 5.163 | 3.307 | 64.05% | 2.25% |
| 26 | 25% | 70.4% | 29.6% | 0% | 0.800 | 5.163 | 3.252 | 62.98% | 0.22% |
| 27 | 35% | 70.4% | 29.6% | 0% | 0.800 | 5.163 | 3.238 | 62.71% | 0.22% |
| 28 | 40% | 70.4% | 29.6% | 0% | 0.800 | 5.163 | 3.324 | 64.38% | 0.11% |
| 29 | 45% | 70.4% | 29.6% | 0% | 0.800 | 5.163 | 3.420 | 66.24% | 0.05% |
| 30 | 50% | 70.4% | 29.6% | 0% | 0.800 | 5.163 | 3.442 | 66.67% | 0.17% |
| 31 | 15% | 59.0% | 31.0% | 10% | 0.800 | 4.908 | 3.127 | 63.71% | 0.17% |
| 32 | 25% | 59.0% | 31.0% | 10% | 0.800 | 4.908 | 3.110 | 63.36% | 0.37% |
| 33 | 35% | 59.0% | 31.0% | 10% | 0.800 | 4.908 | 3.116 | 63.49% | 0.15% |
| 34 | 40% | 59.0% | 31.0% | 10% | 0.800 | 4.908 | 3.166 | 64.51% | 0.09% |
| 35 | 45% | 59.0% | 31.0% | 10% | 0.800 | 4.908 | 3.242 | 66.06% | 0.53% |
| 36 | 50% | 59.0% | 31.0% | 10% | 0.800 | 4.908 | 3.249 | 66.19% | 0.17% |
| 37 | 55% | 590.0% | 31.0% | 10% | 0.800 | 4.908 | 3.238 | 65.98% | 0.83% |

Figure 5:
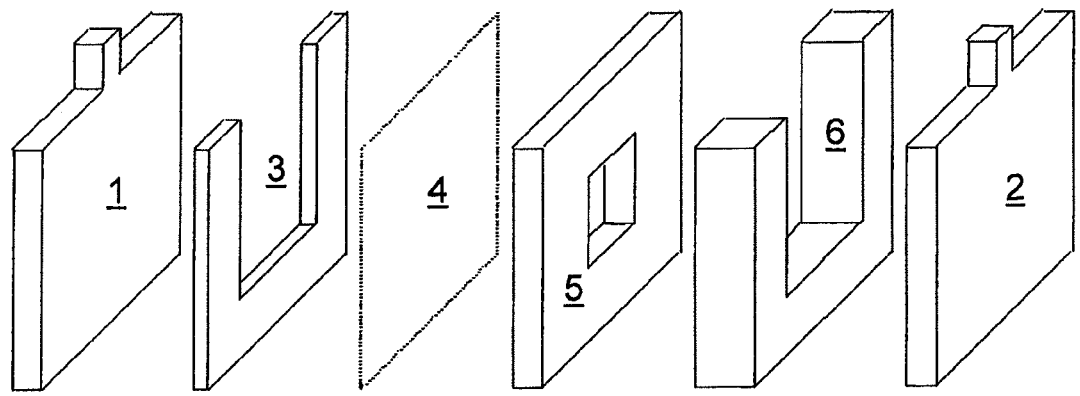
FIG. 5 An exploded view of the schematic configuration of the cell for the precipitation by electrophoresis, using the membrane electrophoresis.

The precipitating out occurred with the aid of membrane electrophoresis. For the purpose of this embodiment, FIG. 5 shows an exploded view of a possible schematic configuration of the cell for the precipitation by electrophoresis. The following components in a layered arrangement are positioned between an anode 1 and a cathode 2, starting from the anode: a compensating chamber 3 (plastic, layer thickness approx. 2 mm), a membrane 4, a forming window 5 (plastic, layer thickness approx. 5 mm), a suspension chamber 6 (plastic, layer thickness approx. 10 mm). For this example, the forming window for precipitating out the green body measures approx. 3 to 5 cm$^2$.

Regenerating cellulose surfaces (e.g. with a wall thickness of 20 to 50 μm) are preferably used for the membranes, such as the ones known from the dialysis technology. In addition to the use of film-type, non-structured membranes, the use of form-stable, non-structured and structured membranes composed of various materials is also proposed. These are preferably produced by casting and curing of a liquid mixture of the following materials:

PMMA-MMA: polymethylmethacrylate particles (scientific Polymer 037D, MW 540.000; $d_{50}$=90 μm) are mixed with methylmethacrylate (MMA, Co. Sigma Aldrich), DI water and Walloxen NO 40 (nonylphenolethoxylate with 4 ethylene oxide groups; Co. Wall Chemie) and are poured, so that a porous frame develops during the polymerization.

Deguvest CF (Co. Degussa): phosphate-bound matrix Mg$_3$(PO$_4$)$_2$, which is prepared with a special mixing fluid and is then cured.

Super hard plaster (Co. Wieland Dental+Technik): dental plaster mixed with de-ionized (DI) water and subsequently cured.

The larger of the two cell chambers, comprising the suspension chamber 6 and the forming window 5, is filled with the suspension for precipitating out while the smaller compensation chamber 3 is filled with a compensating liquid consisting of diluted, watery TMAH solution (tetramethylammoniumhydroxide solution). The conductivity ratio of compensation liquid to suspension must be adjusted to a specific value, preferably 10. This is advantageously achieved by adding TMAH to the compensation liquid. The membrane 4 was infiltrated with DI water to prevent undesirable gas reservoirs.

The electrical field intensity that exists at the electrodes 1, 2 during the precipitation was adjusted to range from 5 to 25 V/cm. The duration of the precipitation ranges from 1 to 5 min for the precipitation on a flat membrane and increases to up to 10 min for the precipitation on structured membranes. The cell is then taken apart and the green body removed from the forming window.

Maintaining the pH values, especially those of the TMAH stabilized suspensions, is absolutely necessary for the precipitation. An increase in the bubble formation can be observed with increasing pH values. On the other hand, the stability of the suspension is reduced for pH values lower than 7 and thus the effectiveness and realization of the precipitation. For that reason, pH values between 7 and 8 have proven to be most suitable for TMAH stabilized suspensions.

A citric acid containing dispersing agent can be used for an alternative stabilization. With sufficiently high dispersing agent content, no further change in the pH value is required for the stabilization. With the aid of rheological measurements, the optimum dispersing agent content was determined to be in the range of 300 to 400, preferably approx. 350 μg/m$^2$ particle surface.

A stabilization with CE-64 on the other hand advantageously does not require that a specific pH value range is precisely maintained.

Watery ceramic suspensions of different compositions, composed of zirconium disilicid, zirconium oxide and a nanoscale silicon oxide as inorganic binder, were also produced and precipitated out with electrophoresis. The admixture of nanoscale SiO$_2$ resulted in increased strength of the green body, which is preferred to be sure and also facilitates the handling, but is not absolutely necessary. The green density of the precipitated out green bodies was subsequently determined and, in the process, the dependence on the material composition as well as the solid content of the suspension determined.

The green densities for the suspension compositions disclosed within the framework of the realized embodiment are listed in Table 3.

Figure 6:
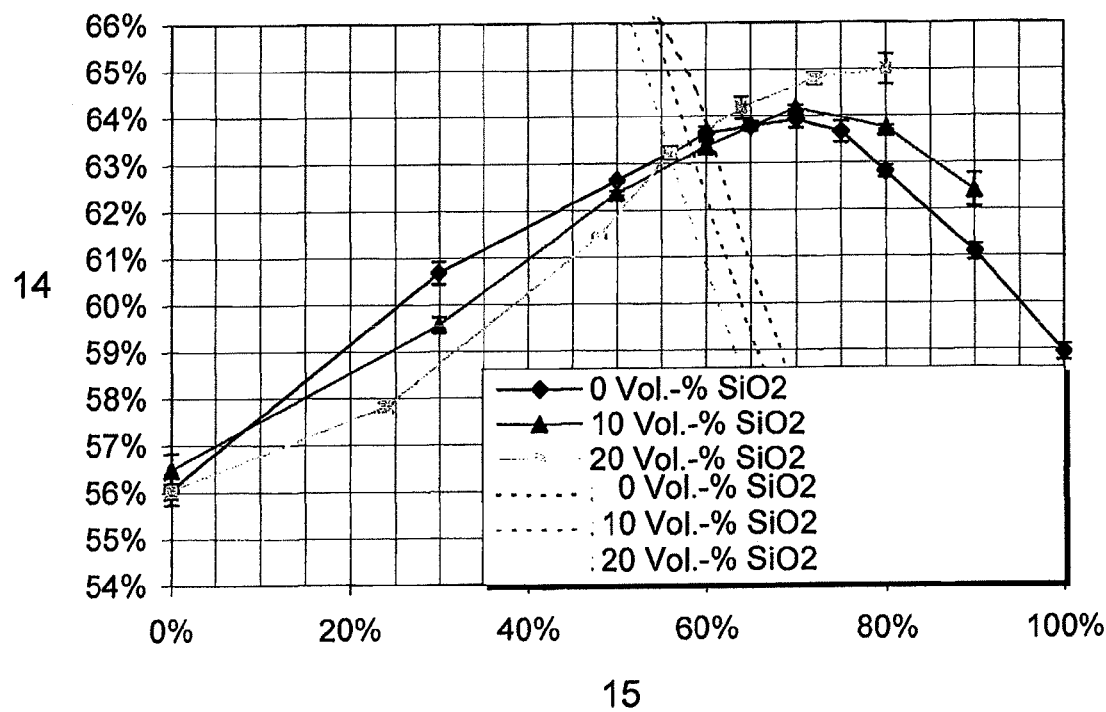
FIG. 6 The relative green densities of molded bodies precipitated out by electrophoresis, as a function of the green body composition.

The dependence of the green density on the individual factors is shown graphically in FIG. 6 for a 35% by volume suspension. FIG. 6 shows the relative green densities 14 [% theoretical density] in reference to the volume share 15 [%] of $ZrSi_2$ to $ZrSi_2+ZrO_2+0.10$ and 20% by volume $SiO_2$ (meaning not applied to the complete solid material content). Also drawn in are the required green densities for the respective $SiO_2$ content to achieve a shrinkage-free sintering with the given composition for the suspension (legend: "DV=0"). These curves were computed analytically based on the phase shares and the expected densities following the sintering. Thus, only material compositions for which the curves of the measured and the required green density intersect can be considered for a shrinkage-free sintering. For the present example, these apply to mixing ratios of $ZrSi_2/ZrO_2/SiO_2$ of approximately:

60/40/0% by volume
58/32/10% by volume
56/24/20% by volume

Figure 7:
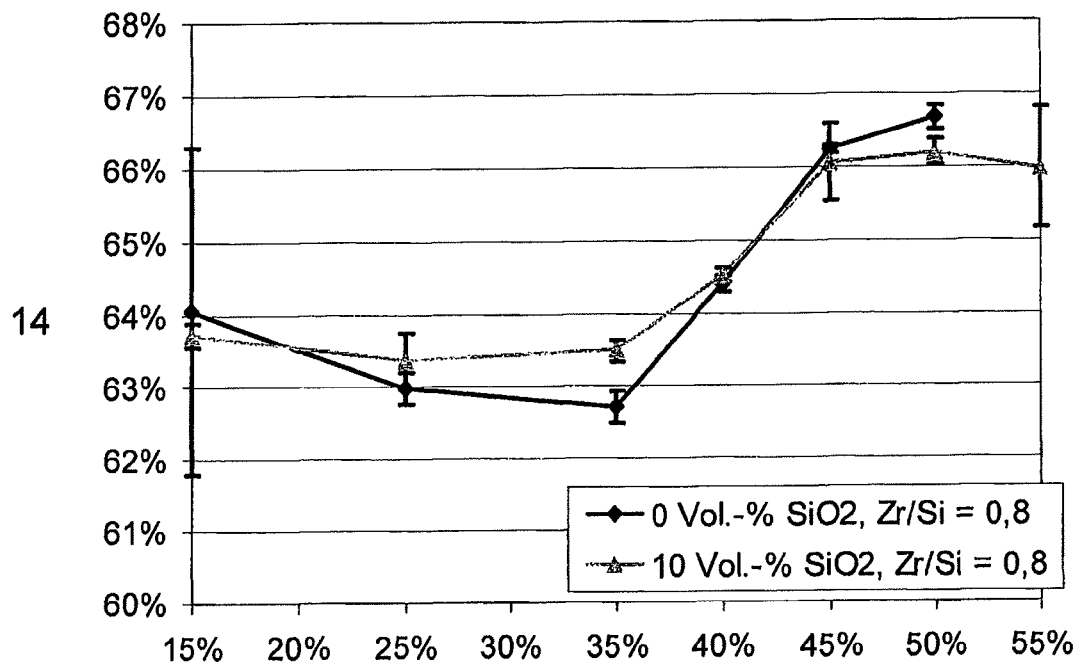
FIG. 7 The relative green densities in dependence on the solid material content.

Additional flexibility for varying the material can be achieved to a small degree by adapting the solid material content. FIG. 7 shows the relative green densities 14 [% theoretical density] in dependence on the solid material content 11 [% vol.]. With a solid material content below 35% by volume, the green density determined with examples for green bodies with a Zr/Si ratio of 0.8, is in the range of 63 . . . 64% of the theoretical density. If the solid material content is increased to at least 40, preferably 45 to 55 or 60% by volume, an increased and thus preferred green density of approximately 66% of the theoretical density will adjust.

To determine whether the composition of the green bodies also corresponds to the composition of the suspension, the $ZrSi_2$ content was determined with the gravimetric method, wherein precipitated out molded bodies were finely ground and the powder subsequently oxidized at 1600° C. for 4 hours. The $ZrSi_2$ content can be determined based on the mass increase and, in all cases, was within the framework of the measuring error at 100±% of the $ZrSi_2$ content of the suspension.

The unmolding from structured membranes preferably occurs following a short-time pole reversal between the electrodes 1, 2. Preferably the pole reversal occurs at the same electrical field intensity as applied during precipitation. This causes the foreign substance on the membrane to loosen up, so that the molded green body can be removed easier. An earlier drying (e.g. through convective heating and/or vacuum pressure) of the green body alternatively facilitates the removal from the forming window 4. As a result of a suspended position, the molded body can also unmold itself as a result of its inherent weight. The hydrophobization of a preferably structured membrane surface, e.g. with the aid of a thin film of paraffin, also makes it harder for the green body to adhere and thus facilitates the unmolding.

For this exemplary embodiment, the green bodies precipitated out by electrophoresis are oxidized following the unmolding and are then sintered. The temperature program was adapted such that a complete oxidation is ensured in the lower temperature range and good sintering is ensured in the upper temperature range. The following results were achieved for a suitable, not time-optimized oxidation temperature program:

$$0 \xrightarrow{5} 480 \xrightarrow{1.2} 600 \xrightarrow{0.25} 650 \xrightarrow{0.15} 760 \xrightarrow{1} 840 \xrightarrow{4} 1100.16\ h \qquad (1)$$

The program provides for a temperature increase with different heating rates (numbers above the arrows in [K/min]) via different intermediate temperatures (in [° C.]) up to 1100° C. This temperature is maintained for a period of 16 hours before the sintering is initiated with the following sintering program:

$$1100 \xrightarrow{5} 1275,\ 16\ h \xrightarrow{5} 1300,\ 16\ h \xrightarrow{5} 1325,\ 16\ h \xrightarrow{5} 1575,\ 4\ h \qquad (2)$$

At the end of the four-hour holding period, the green body which has been converted to a sintered body is cooled at a cooling rate of 10 K/min to the room temperature.

Figure 8:
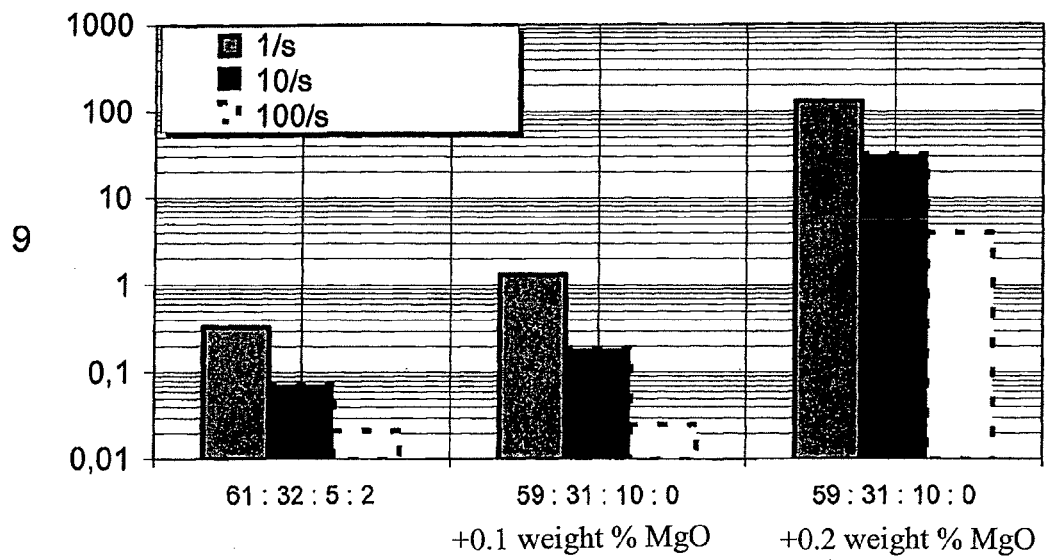
FIG. 8 The viscosity of 35% by volume suspensions with differing compositions ($ZrSi_2$:$ZrO_2$:$SiO_2$:$MgAl_2O_4$)

Sintering additives are required for a reliable sintering of the green bodies. Based on experience, aluminum oxide and magnesium oxide in particular are suitable for this. However, when producing MgO-containing watery suspensions, it was found that starting with the admixture of approximately 0.1% by weight of MgO, the viscosity increases rapidly after a short time, which makes a precipitation by electrophoresis impossible. FIG. 8 shows the viscosity 9 in [Pas] in dependence on the composition 16 [% by volume] of $ZrSi_2:ZrO_2:SiO_2:MgAl_2O_4$ at respective low shearing rates, such as is relevant for the precipitation by electrophoresis. The two compositions shown on the right additionally contain 0.1 and 0.2%, respectively, by weight of MgO.

This viscosity-increasing effect does not occur when using spinel ($MgAl_2O_4$). Suspensions containing up to 2% by volume spinel (FIG. 8, composition shown on the left) were precipitated out by electrophoresis and then sintered without the aforementioned effect.

Following the sintering, the volume change was determined as compared to the green body, using on the one hand the knowledge of the absolute mass increase of $ZrSi_2$, its percentage share in the molded body, as well as the absolute green density and sintering density. On the other hand, parallel-face discs were cut from the green bodies to compare their lengths in the green state and the sintered state. A remaining increase in length of 1.07% with a standard deviation of 0.57% (from 5 different samples) was determined in the process from a molded body computed to be without shrinkage.

Table 4 shows the empirically measured, relative length changes (sintering shrinkages) of sintering samples with a composition of 55:33:10:2% by volume ($ZrSi_2:ZrO_2:SiO_2:MgAl_2O_4$) in different measuring directions. The sintered sample body in this case has square or cube-shaped surface structures, for which the edge length (edges), diagonal length and the height (vertical line) can be measured reliably. The analyzed molded body with the specified material composition does not exhibit shrinkage within the framework of the measuring accuracy. However, the standard deviations are extremely high, especially for the vertical measurement.

TABLE 4 relative change in length of sintered bodies
as compared to the green bodies for the composition 55:33:10:2
% by volume ($ZrSi_2$:$ZrO_2$:$SiO_2$:$MgAl_2O_4$) in
different measuring directions.

| measuring direction | change in length |
|---|---|
| edges | 0.21% ± 0.62% |
| diagonal | 0.08% ± 0.62% |
| vertical | 0.15% ± 1.48% |

Ethanol was tested as possible dispersing agent (liquid used as basis for the suspension) in addition to water. An extremely high viscosity was observed for a suspension of 35% by volume. At a shearing rate of 1/s, the viscosity was already clearly above 100 Pas, which is no longer tolerable for the precipitation by electrophoresis. The initially mentioned dispersing agent containing citric acid, as well as a trioxide decanoic acid were tested for the stabilization.

Figure 9:
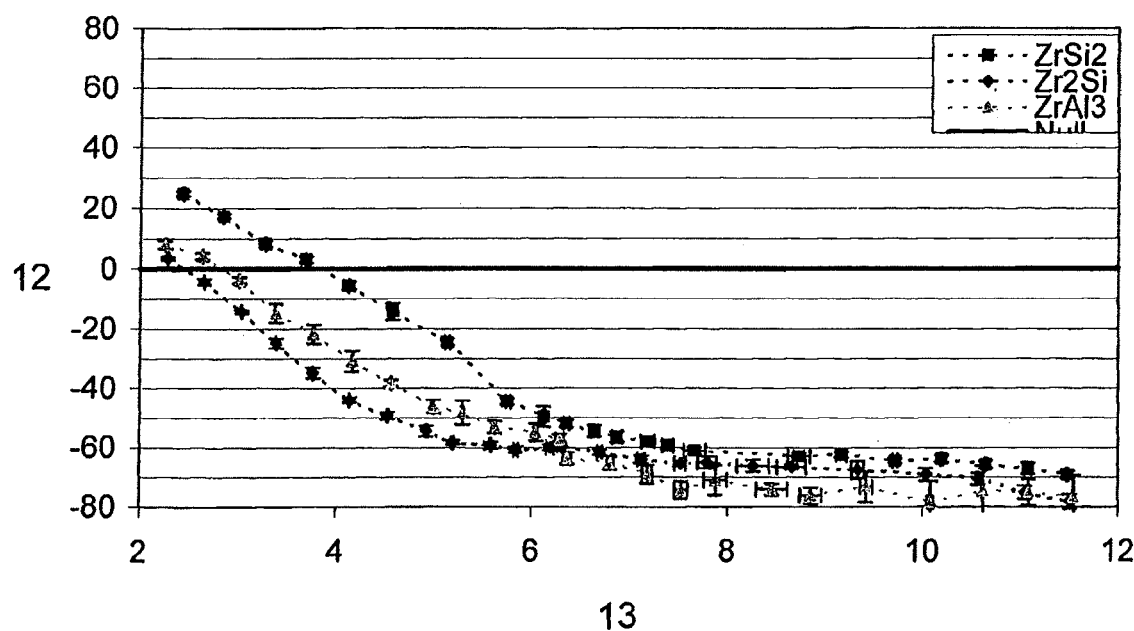

In principle, the invention also includes other inter-metallic powder fractions in place of the $ZrSi_2$ used for this example. In particular dizirconiumsilicid ($Zr_2Si$) and zirconium aluminid ($ZrAl_3$) are mentioned as examples. FIG. 9 shows the zeta potentials 12 in [mV] in dependence on the dimensionless pH values 13 in the same way as in FIG. 4a. As can be seen, the aforementioned inter-metallic powder fractions (dizirconiumsilicid, zirconiumaluminid) have zeta potential courses that are basically similar to those of the $ZrSi_2$ and are thus suitable for use as inter-metallic compounds within the framework of the invention. This was verified with the aid precipitation by electrophoresis, wherein the precipitation occurred without problem using $Zr_2Si$ containing suspensions (82% by volume $Zr_2Si$; 10% by volume $SiO_2$; 6% by volume $ZrO_2$ and 2% by volume spinel) to which a citric acid containing dispersing agent was added. The same was true for the precipitation with $ZrAl_3$ containing suspensions (70% by volume $ZrAl_3$; 18% by volume $ZrSi_2$; 10% by volume $SiO_2$ and 2% by volume spinel), wherein a sodium dispersing agent was used in addition to the citric-acid containing dispersing agent.

The precipitation from $ZrAl_3$ containing suspensions is possible also in connection with stabilization via the pH value. However, it must be noted that the stability of the suspensions is poorer than with the use of dispersing agents, so that dispersing agents are preferable to a pH stabilization. Successfully tested were pH values of 8.9 (intrinsic pH value without admixture of acids/bases), 9.7 and 10.9. A decrease in the rate of precipitation can be observed with an increase in the pH value because of the increase in the conductivity.

The green densities that can be achieved with the $Zr_2Si$ containing suspension are approximately 59.1% theoretical density and with the $ZrAl_3$ containing systems are 57.1% (citric-acid containing dispersing agent), 57.9% (Darvan), and/or 55.1% (stabilized via pH value). They are clearly below the green densities that can be achieved with the tested $ZrSi_2$ containing suspensions. In the final analysis, it means that a clearly higher share of inter-metallic compounds must be used to obtain a shrinkage-free reaction sintering.

It will be understood that the above description of the present invention is susceptible to various modifications, changes and adaptations, and the same are intended to be comprehended within the meaning and range of equivalents of the appended claims.

What is claimed is:

1. A method for producing ceramic components, comprising:
   providing a dispersion comprising at least one first and one second powder fraction of an oxide ceramic, and a third powder fraction of an inter-metallic compound mixed in a liquid, wherein the first powder fraction comprises a nanoscale particle fraction with particle sizes ranging from about 2 nm to about 200 nm and functions as a binder, the second powder fraction comprises a sintering additive, and the share of the third powder fraction, relative to the sum of all powder fractions, has a volume share of between about 50% and about 95%;
   forming a green body by precipitating the powder fractions from the mixture with the aid of electrophoresis; and
   sintering of the green body in an oxidizing atmosphere to form a ceramic component.

2. The method according to claim 1, wherein the liquid is a non-watery liquid.

3. The method according to claim 1, wherein the liquid is a watery liquid and the method includes adjusting a pH value of between about 5 and about 10 in the dispersion for the precipitation by electrophoresis.

4. The method according to claim 1, including stabilizing the dispersion with a neutral dispersing agent.

5. The method according to claim 4, wherein the stabilizing includes adjusting the share of dispersing agent per powder surface to a range from about 200 μg/m$^2$ to about 4000 μg/m$^2$.

6. The method according to claim 1, wherein the first and the third powder fractions have a bimodal size distribution.

7. The method according to claim 6, wherein the third particle fraction contains particle sizes ranging from about 0.2 μm to about 10 μm, and the ratio of the average particle size for the third powder fraction to that of the first powder fraction is between about 2.5 and about 250.

8. The method according to claim 1, wherein the sintering additive includes a $MgAl_2O_4$ spinel.

9. The method according to claim 1, wherein a solid material share of the first to the third particle fraction in the dispersion ranges from about 1% to about 60% by volume prior to the precipitation.

10. The method according to claim 1, wherein the providing includes providing the dispersion with additional powder fractions comprised of at least one of a metal or oxide ceramic.

11. A method for producing ceramic dental components or micro components, comprising utilizing the method according to claim 1.

* * * * *